(12) United States Patent
Berberich et al.

(10) Patent No.: US 8,075,588 B2
(45) Date of Patent: Dec. 13, 2011

(54) DEVICE FOR INSERTING AN ANCHORING ELEMENT AND A SUTURE THREAD INTO A BONE

(75) Inventors: Sascha Berberich, Tuttlingen (DE); Ina Baltes, Tuttlingen (DE)

(73) Assignee: Karl Storz GmbH & Co. KG (DE)

( * ) Notice: Subject to any disclaimer, the term of this patent is extended or adjusted under 35 U.S.C. 154(b) by 474 days.

(21) Appl. No.: 11/418,442

(22) Filed: May 4, 2006

(65) Prior Publication Data

US 2006/0253119 A1 Nov. 9, 2006

(30) Foreign Application Priority Data

May 4, 2005 (DE) .................. 10 2005 021 885

(51) Int. Cl.
*A61B 17/04* (2006.01)
*A61B 17/58* (2006.01)
(52) U.S. Cl. ........................ 606/232; 606/104
(58) Field of Classification Search .................. 606/232, 606/99, 104; 623/2.11
See application file for complete search history.

(56) References Cited

U.S. PATENT DOCUMENTS

| | | | |
|---|---|---|---|
| 4,632,100 A | 12/1986 | Somers et al. ............... 128/92 |
| 5,569,252 A | 10/1996 | Justin et al. ................. 606/73 |
| 5,690,676 A * | 11/1997 | DiPoto et al. ................ 606/232 |
| 5,766,250 A * | 6/1998 | Chervitz et al. ............ 606/232 |
| 6,503,251 B1 * | 1/2003 | Shadduck ..................... 606/311 |
| 6,508,830 B2 * | 1/2003 | Steiner ........................ 606/232 |
| 6,592,610 B2 * | 7/2003 | Beyar .......................... 606/232 |
| 6,818,010 B2 * | 11/2004 | Eichhorn et al. ............ 606/232 |
| 6,932,834 B2 * | 8/2005 | Lizardi et al. .............. 606/232 |
| 2003/0144696 A1 * | 7/2003 | Sinnott et al. .............. 606/232 |
| 2004/0243178 A1 * | 12/2004 | Haut et al. .................... 606/232 |
| 2006/0030884 A1 * | 2/2006 | Yeung et al. ................ 606/232 |

* cited by examiner

*Primary Examiner* — Corrine M McDermott
*Assistant Examiner* — Christina Lauer
(74) *Attorney, Agent, or Firm* — St. Onge Steward Johnston & Reens LLC

(57) ABSTRACT

A device serves to insert an anchoring element and a suture thread into a bone to attach a tendon or a ligament without drilling a hole into the bone. The device comprises an anchoring element, having a proximal end, a distal end, and a longitudinal axis and further a continuous channel, and a tool for inserting the anchoring element and the suture thread, having a longitudinal axis, a distal end section and a further section being designed in such a way that it can be introduced into the anchoring element from the proximal end to the distal end. The tool can be inserted into the continuous channel of the anchoring element in such a way that the distal end section of the tool projects distally beyond the anchoring element, wherein the projecting distal end section is designed as a stable driving head. The anchoring element further has an external thread.

13 Claims, 5 Drawing Sheets

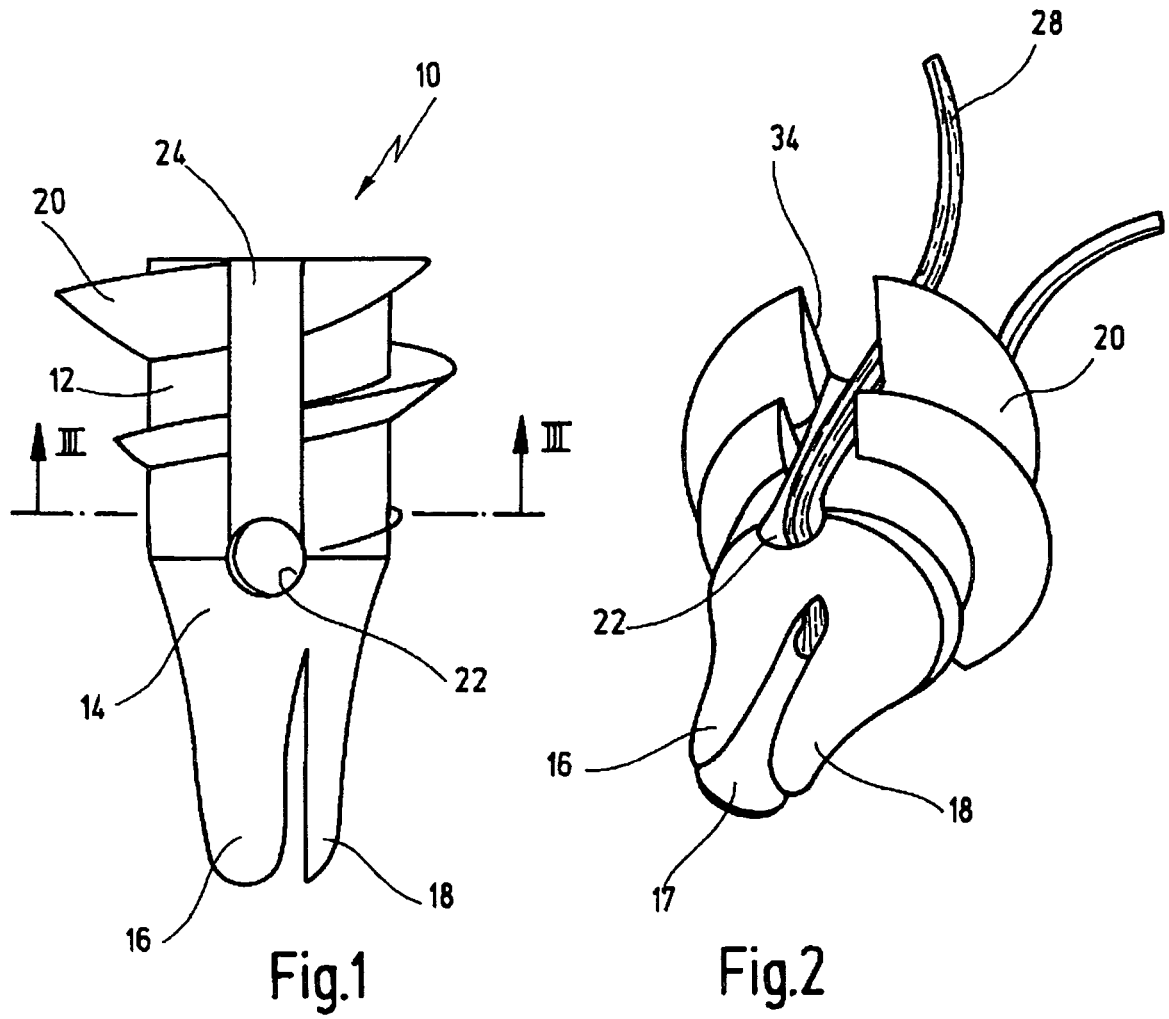

DEVICE FOR INSERTING AN ANCHORING ELEMENT AND A SUTURE THREAD INTO A BONE

BACKGROUND OF THE INVENTION

The invention relates to a device for inserting an anchoring element and a suture thread into a bone to attach a tendon or a ligament without drilling a hole into the bone.

Anchoring elements of this kind are anchored in a bone together with a suture thread, and a torn tendon or ligament is reattached to the bone with the suture thread.

One of the main applications for such anchoring elements is the attachment of torn tendons in the shoulder area.

Two types of procedure have become established in this technology.

In the first type of procedure, a channel is drilled into the bone, and the anchoring element with the suture thread is introduced into this predrilled channel. For this, the anchoring element is mounted on a tool and driven into the drill hole with this tool. Once the anchoring element is in place, the tool is removed, and the tendon is attached using the ends of the suture thread which project from the drill hole. The outside of the anchoring element has hook-like or barb-like projections to anchor the anchoring element in the drill hole.

U.S. Pat. No. 5,690,676 describes a design in which the anchoring element has a continuous channel by means of which a guide wire can be pushed through the anchoring element such that a distal end section of the guide wire projects beyond the anchoring element. This projecting section serves as an aid for targeting and inserting, particularly in cases where the anchoring elements are small or the drill holes are very small. This means the wire is inserted into the drill hole in the bone, and the anchoring element is then advanced along the wire and into the drill hole. The wire is then withdrawn, the tool attached, and the previously described driving in operation effected.

With this technology it is absolutely essential to drill a hole in the bone beforehand.

U.S. Pat. No. 4,632,100 describes a device for inserting an anchoring element which can be used without drilling a hole first.

Here, the distal tip of the anchoring element itself is designed as a driving head. For this, the anchoring element must be very sturdy and, in particular, must be made of metal. In addition, the outside of the anchoring element has an external thread so that once the anchoring element has been knocked in it can be anchored in the bone with a turning movement by means of the external thread. A tool is attached to the proximal end of the anchoring element for this operation. Here too a suture thread can be introduced at the same time.

The drawback of this design is that the anchoring element needs to be very sturdy, very complex, and, in particular, has to be made of metal and remains in the body as a metallic foreign body.

Knock-in anchors of this kind cannot be used for osteoporotic bones. Furthermore, attempts are being made to use absorbable materials which can gradually be replaced by endogenous bone tissue. However, since absorbable materials do not have sufficient mechanical stability, it is not possible to use knock-in anchors made of such materials.

SUMMARY OF THE INVENTION

It is therefore an object of the present invention to create a device of the type mentioned at the start which does not require the drilling of a hole but also allows the anchoring element to be constructed of absorbable materials.

In accordance with an aspect of the invention a device for inserting an anchoring element and a suture thread into a bone to attach a tendon or ligament without drilling a hole in the bone is provided, comprising an anchoring element having a proximal end, a distal end and a longitudinal axis and further having a continuous channel and an external thread. The device further comprises a tool for inserting the anchoring element and the suture thread, having a longitudinal axis, a distal end section and a further section being designed in such a way that it can be introduced into the anchoring element from the proximal end to the distal end, the tool being able to be inserted into the continuous channel of the anchoring element in such a way that the distal end section of the tool projects distally beyond the anchoring element, the projecting distal end section being designed as a stable driving head.

The fact that the section of the tool which projects distally beyond the anchoring element is designed as a stable driving head means that it is now possible to drive this assembly in like a knock-in anchor without drilling a hole first. However, it is not the distal tip of the anchoring element that is driven in, but only the distal section of the tool that projects beyond the anchoring element. This must have adequate strength and rigidity and must also be made of metallic materials.

The provision of the external thread on the outside of the anchoring element means that, once the distal tip of the tool has been knocked in, the anchoring element/tool assembly can be turned and the anchoring element can be screwed into the opening created by the knocking-in and can be secured in place by means of the external thread. After this operation the tool is removed and the anchoring element is left firmly anchored in the bone without there having been a need to drill a hole first and without the anchoring element having to be constructed of stable and, in particular, metallic materials.

In a further embodiment of the invention the tool is accommodated in the anchoring element in a rotationally locked manner.

The advantage of this arrangement is that this rotational locking makes the turning movement effected when screwing in the thread of the anchoring element easy to perform.

In a further embodiment of the invention the tool has a tip at a distal end section.

The advantage of this arrangement is firstly that the surgeon is able to precisely target the contact site or knock-in point with the aid of the tip and furthermore that the distal end section of the tool formed as a stable driving head can be driven in gently.

In a further embodiment of the invention the anchoring element comprises a distal taper.

The advantage of this arrangement is that the anchoring element, sliding smoothly over this taper, can be driven into the bone during the initial driving in operation.

In a further embodiment of the invention the taper is designed in such a way that it is continued by the tip of the tool.

This arrangement has the particular advantage that there is a smooth transition from the distal end of the anchoring element to the tip of the tool projecting beyond the anchoring element, with the result that driving in operation can be carried out in a particularly nondisruptive manner.

In an embodiment of the invention the external thread of the anchoring element extends over roughly the rear, proximal half of the anchoring element.

The advantage of this arrangement is that the anchoring element can first be driven or knocked into the bone to a certain extent in a linear driving in operation and that the external thread only then screws into the bone.

In a further embodiment of the invention the external thread of the anchoring element extends over the entire length of the anchoring element.

The advantage of this arrangement is that in the case of particularly porous bones, when anchoring over the whole of the outside of the anchoring element is necessary, this can be effected via this external thread which extends over the entire body.

In a further embodiment of the invention the section of the tool that can be inserted into the anchoring element has a cross-sectional profile which is roughly the shape of a three-pointed star.

The advantage of this arrangement is that this geometry makes it possible to achieve a rotationally locked connection with a very large area of contact with the anchoring element, such that even high torque does not cause the anchoring element to deform or shear off.

In a further embodiment of the invention the section of the tool which is inserted in the anchoring element has a cross-sectional profile which is roughly the shape of a figure eight.

The advantage of this arrangement is that this too allows the creation of a rotationally locked connection with a relatively large area of contact and that in the middle of the eight there is a space for the suture thread on both sides.

In a further embodiment of the invention the anchoring element has a continuous opening to accommodate the suture thread, this opening running transverse to the longitudinal axis of the anchoring element.

The advantage of this known arrangement is that the suture thread passes once, transversely, right through the anchoring element, this providing the appropriate support by which the suture thread can then be firmly connected to the tendon.

In a further embodiment of the invention the position of the end point of the tip of the tool is radially offset relative to the central longitudinal axis of the tool.

As mentioned earlier, the suture thread is passed once, transversely, right through the anchoring element, i.e. diametrically. The lateral offset of the tip prevents the tip from hitting the suture thread—it pushes past the suture thread because of the lateral offset—and prevents it from getting caught or stuck on the suture thread.

In a further embodiment of the invention the continuous opening passes into grooves which run axially, in a proximal direction, along the outside of the anchoring element and which serve to accommodate the suture thread.

The advantage of this arrangement, which is also known per se, is that the suture thread can be guided in a proximal direction along the outside. The grooves extend through the thread, so that the suture thread is not damaged when the anchoring element is driven in beyond the thread section.

In a further embodiment of the invention the tool has grooves which continue the grooves of the anchoring element in a proximal direction and which serve to accommodate the suture thread axially.

The advantage of this arrangement is that the orientation of the grooves allows the suture thread to be guided in a proximal direction, along the outside of the anchoring element/tool assembly, on both sides.

In a further embodiment of the invention the tool has a catching slit in the section which is inserted into the anchoring element to accommodate the suture thread.

The advantage of this arrangement is that the suture thread inserted in the anchoring element is captured by the catching slit and held in the tool in a defined way.

In a further embodiment of the invention the catching slit opens to one side of the tool.

The advantage of this arrangement is that, when the tool is pushed in, the suture thread in the continuous opening in the anchoring element is moved to one side—specifically by the laterally offset tip—and then automatically threaded, or slid, into the catching slit.

In a further embodiment of the invention one end of the catching slit of the tool comes to rest at the level of the continuous opening of the anchoring element when the tool has been introduced into the anchoring element.

The advantage of this arrangement is firstly that the tool brings the suture thread into a precisely predetermined position in the anchoring element, i.e. in exact alignment with the lateral openings by which the suture thread passes through the anchoring element.

At the same time this construction also allows the possibility of first inserting the tool into the anchoring element and then, by aligning the opening and the end of the catching slit, of threading the suture thread through the assembly.

In a further embodiment of the invention the tool has a shoulder which comes to rest on a corresponding shoulder on the anchoring element.

The advantage of this arrangement is that the depth of insertion of the tool into the anchoring element is precisely limited, namely when the opposing shoulders are in contact with one another.

It will be appreciated that the features mentioned above and those still to be explained below can be used not only in the described combinations but also in other combinations or on their own without departing from the scope of the present invention.

BRIEF DESCRIPTION OF THE DRAWINGS

The invention is described and explained in greater detail below with the aid of a selected exemplary embodiment in conjunction with the attached drawings, in which:

FIG. 1 shows a lateral view of an anchoring element according to the invention, FIG. 2 shows a lateral perspective view of the anchoring element of FIG. 1 with a suture thread inserted.

DETAILED DESCRIPTION OF THE INVENTION

Figure 3:
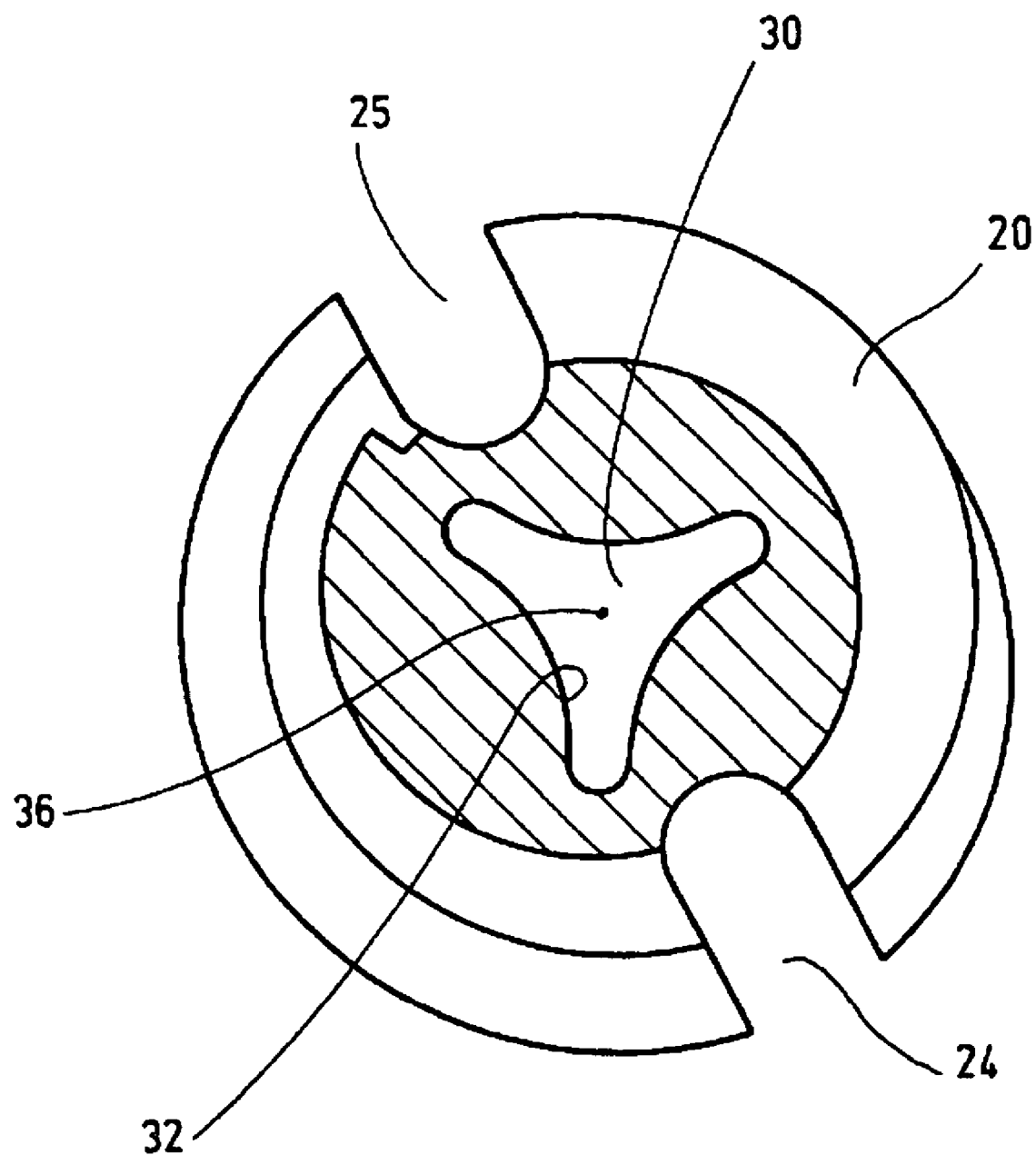
FIG. 3 shows a section along the line III-III of FIG. 1.

FIGS. 1 to 3 show an anchoring element which as a whole is designated with the reference number 10.

The anchoring element 10 has a roughly cylindrical body 12, which distally changes into a taper 14.

The taper 14 is made up of three segments 16, 17, and 18 which are uniformly distributed around the circumference.

The outside of the cylindrical body 12 has a thread 20.

At the point where the cylindrical body 12 joins the taper 14, there is a continuous transverse opening 22.

Extending in a proximal direction from the opening 22 and lying diametrically opposite each other are grooves 24 and 25, which extend right through the thread 20 and emerge at the proximal end.

As FIG. 2 shows, a suture thread 28 can be pushed through the opening 22 and inserted in the grooves 24 and 25 such that the two free ends of the suture thread 28 extend away from the anchoring element 10 in a proximal direction. The suture thread runs diametrically through the anchoring element 10.

The sectional illustration in FIG. 3 shows that extending through the middle of the anchoring element 10 there is a continuous channel 30, which in the area of the cylindrical body 12 has a cross-section 32 with the shape of a three-pointed star.

Proximally, the channel 30 terminates in a sloped shoulder 34.

Figure 4:
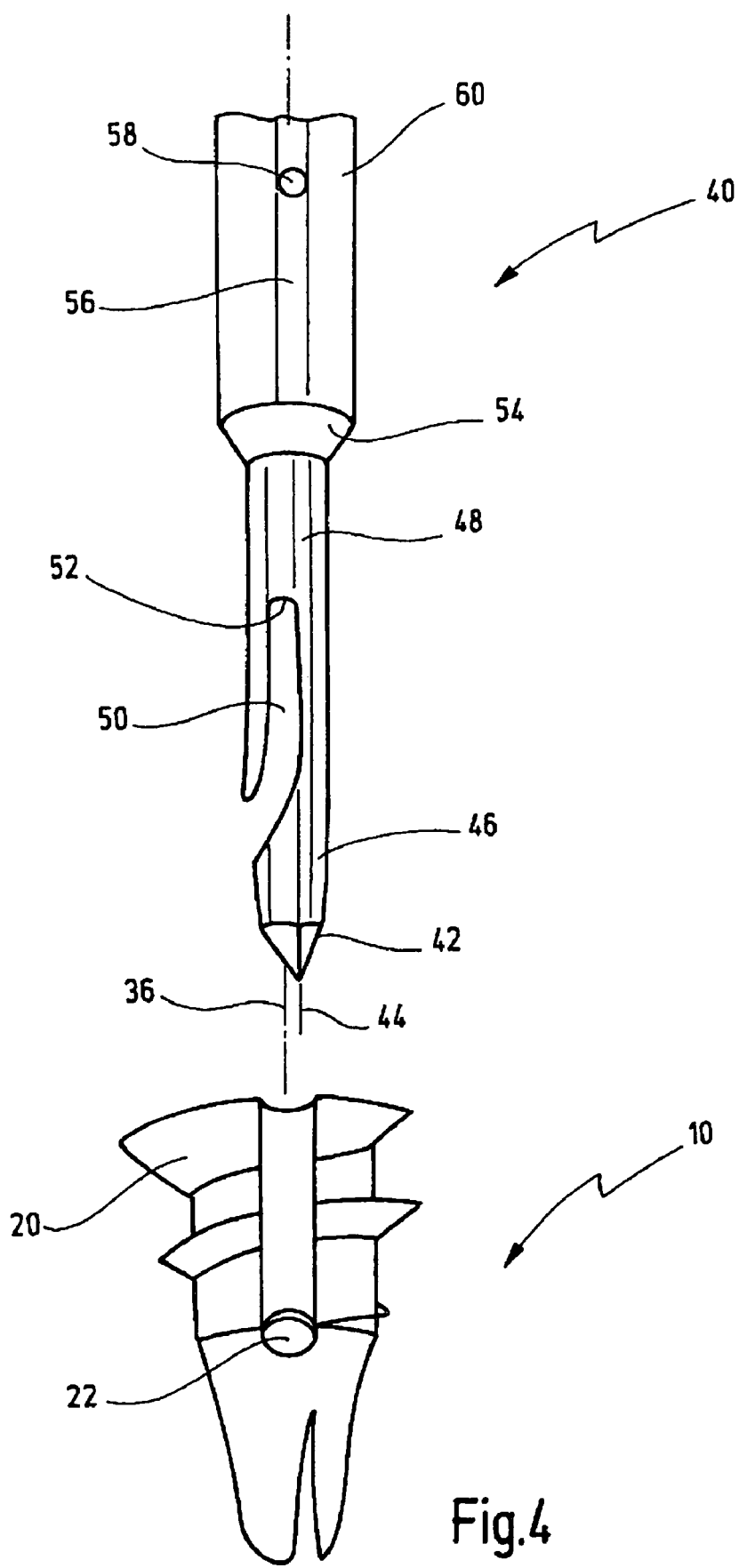
FIG. 4 shows a lateral view of the anchoring element of FIG. 1 and of a distal region of a tool which is to be inserted into the anchoring element from the proximal to the distal position.

As FIG. 4 shows, to insert the anchoring element 10, a tool 40 is inserted from the proximal to the distal position.

Distally, the tool 40 has a roughly pyramid-shaped tip 42, which is relatively sturdy. The external end of the tip 42 is laterally offset relative to the central longitudinal axis 44 of the tool 40 and thus also laterally offset relative to the central longitudinal axis 36 of the anchoring element 10. The tip 42 changes into a section 48 with a cross-sectional profile which likewise has the shape of a three-pointed star.

In other words, section 48 can be inserted in the cross-section 32 of the channel 30 of the anchoring element 10 in a form-fitting and rotationally locked manner.

As FIG. 4 shows, this section 48 has a catching slit 50 which opens to one side, namely the side opposite to the direction of the offset of the tip 42. One end 52 of the catching slit 50 comes to rest at the level of the continuous opening 22 of the anchoring element 10 when the tool 40 is inserted into the anchoring element 10, as described below.

The section 48 changes into a rod-shaped section 60 of the tool 40, via a shoulder 54.

The shoulder 54 is formed in such a way that it can come to rest fittingly against the shoulder 34 at the proximal end of the anchoring element 10, the depth of insertion being accordingly limited or determined.

FIG. 4 also shows that, cut into the outside of the rod-shaped section 60, there are grooves 56, which extend the grooves 24 and 25 found on the anchoring element 10. Projecting radially from each groove 56 is a pin 58 on which to thread or attach the suture thread 28.

Figure 6:
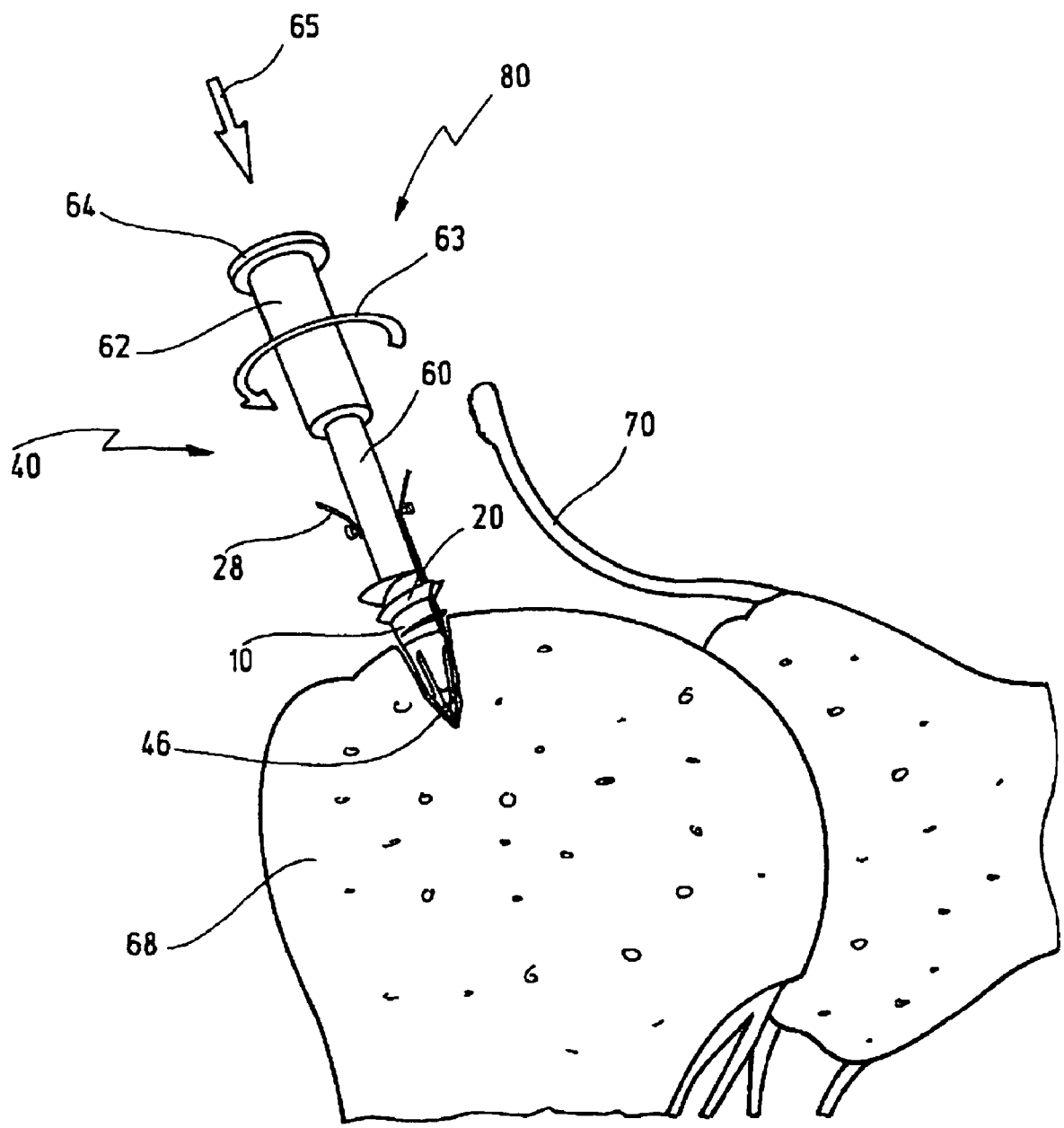
FIG. 6 shows a situation in which the anchoring element is inserted into a shoulder bone using the device according to the invention, consisting of the anchoring element tool/suture thread assembly.

As FIG. 6 shows, the rod-shaped section 60 changes into a handle 62, the end of which has a strike head 64.

To insert the anchoring element 10, the suture thread 28 is first threaded into the anchoring element 10, as shown in FIG. 2.

The tool 40 is then inserted, as shown in FIG. 4. Due to the lateral offset of the tip 42, the tip 42 pushes past the section of suture thread 28 that runs transversely through the anchoring element 10, and the suture thread 28 is automatically guided into the catching slit 50 as the tool 40 is advanced.

Figure 5:
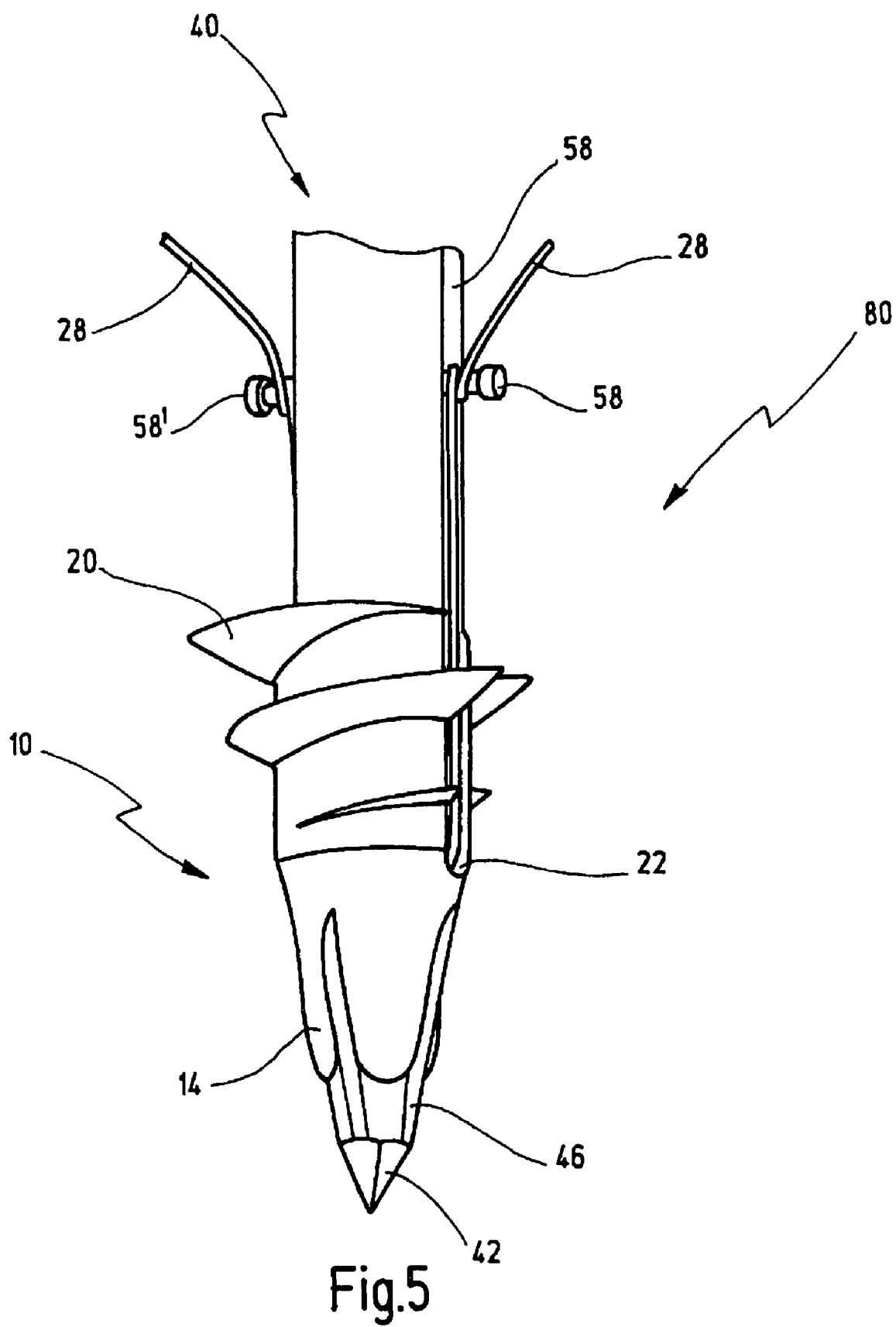
FIG. 5 shows an assembly of the anchoring element and the tool of FIG. 4 together with an inserted suture thread.

Once the tool 40 is fully inserted in the anchoring element 10, as shown in FIG. 5, the suture thread 28 can again be placed tightly and precisely into the grooves 24 and 25 or their extensions 56 on the tool and be attached via the pins 58, 58'.

A distal end section 46 of the tool 40 projects distally beyond the anchoring element 10. The taper 14 or the three segments 16, 17, 18 fit snugly against the contour of this distal end section 46.

The tool 40 is made of a metallic material; the anchoring element 10 is made of an absorbable material.

To insert the anchoring element 10, the tip 42 of the projecting distal end section 46 of the device 80 according to the invention is first brought into contact with a certain site on the bone, e.g. a shoulder bone 68, as shown in FIG. 6, and the device 80, i.e. the assembly of the anchoring element 10 and the tool 40, is first driven in, linearly, as indicated by the arrow 65, using a striking tool.

This driving in operation is continued until the anchoring element 10 has been driven in so far that the distal end section 46 and the taper 14 have been driven in.

Now, by turning the assembly in the manner shown by an arrow 63 in FIG. 6, the assembly is screwed into the bone 68 with the help of the thread 20. The suture thread 28 is protected from displacement or twisting during this operation, since it is contained within the grooves 24, 25 and 56.

Once the anchoring element 10 has been completely screwed into the shoulder bone 68, the tool 40 is withdrawn in a proximal direction, leaving the anchoring element 10 anchored in the bone.

A tendon 70, which has become detached from the shoulder bone 68, can be reattached with the projecting ends of the suture thread 28.

Since no hole has had to be drilled in 68, the anchoring element 10 is in close contact with the bone tissue. Since it is made of absorbable material, it is gradually replaced by bone tissue, resulting in a reattachment of the tendon 70 which resembles the natural state.

What is claimed is:

1. A device for inserting an anchoring element and a suture thread into a bone to attach a tendon or a ligament without drilling a hole into said bone, comprising:
   an anchoring element, having a proximal end, a distal end, and a longitudinal axis, said anchoring element further having a continuous channel and an external thread, said anchoring element further having a continuous opening to accommodate said suture thread, said opening running transverse to said longitudinal axis of said anchoring element, and
   a tool for inserting said anchoring element and said suture thread, having a longitudinal axis, a distal end section and a further section being designed in such a way that it can be introduced into said anchoring element from said proximal end to said distal end,
   said tool being able to be inserted into said continuous channel of said anchoring element in such a way that said distal end section of said tool projects distally beyond said anchoring element, said projecting distal end section being designed as a stable driving head,
   wherein said tool comprises a tip at said distal end section having an end point, said end point of said tip having a position that is radially offset relative to said central longitudinal axis of said tool,
   said tool having a catching slit in said distal end to automatically accommodate said suture thread when inserting said tool into said anchoring element, and
   wherein said suture thread comes free from said catching slit when said tool is withdrawn from said anchoring element, and
   wherein the catching slit opens to a side opposite to a direction of the offset of the tip.

2. The device of claim 1, wherein said tool is accommodated in said anchoring element in a rotationally locked manner.

3. The device of claim 2, wherein said distal end of said tool has a cross-sectional profile having roughly the shape of a three-pointed star.

4. The device of claim 2, wherein said distal end of said tool has a cross-sectional profile having roughly the shape of a figure eight.

5. The device of claim 1, wherein said anchoring element comprises a distal taper.

6. The device of claim 5, wherein said taper is designed in such a way that it is continued by said tip of said tool.

7. The device of claim 1, wherein said external thread of said anchoring element extends over roughly a rear, proximal half of said anchoring element.

8. The device of claim 1, wherein said external thread of said anchoring element extends over an entire length of said anchoring element.

9. The device of claim 1, wherein said anchoring element comprises grooves, which run axially, in a proximal direction, along said outside of said anchoring element and which serve to accommodate said suture thread, said continuous opening passing into said grooves.

10. The device of claim 9, wherein said tool comprises grooves, said grooves continuing said grooves of said anchoring element in a proximal direction, and serving to accommodate said suture thread axially.

11. The device of claim 1, wherein said catching slit opens to one side of said tool.

12. The device of claim 1, wherein said end of said catching slit of said tool coming to rest at level with said continuous opening of said anchoring element when said tool has been introduced into said anchoring element.

13. The device of claim 1, wherein said tool comprises a shoulder and, said anchoring device comprises a shoulder, said shoulder of said tool coming to rest on said shoulder of said anchoring element.

* * * * *